(12) United States Patent
Zettel

(10) Patent No.: US 9,032,581 B2
(45) Date of Patent: May 19, 2015

(54) USE OF A TOOTHPASTE AND A TOOTHBRUSH, A DENTAL CLEANING SYSTEM AND TOOTHBRUSH

(71) Applicant: Roland Zettel, Teufen (CH)

(72) Inventor: Roland Zettel, Teufen (CH)

(73) Assignee: megasmile AG, Tuefen (CH)

( * ) Notice: Subject to any disclaimer, the term of this patent is extended or adjusted under 35 U.S.C. 154(b) by 73 days.

(21) Appl. No.: 14/035,838

(22) Filed: Sep. 24, 2013

(65) Prior Publication Data
US 2014/0082867 A1    Mar. 27, 2014

(30) Foreign Application Priority Data

Sep. 25, 2012 (CH) ........................ 1733/12

(51) Int. Cl.
| | |
|---|---|
| *A46D 1/00* | (2006.01) |
| *A46B 11/00* | (2006.01) |
| *A61Q 11/00* | (2006.01) |
| *A46B 9/04* | (2006.01) |
| *A46B 15/00* | (2006.01) |

(52) U.S. Cl.
CPC ............ *A46D 1/0207* (2013.01); *A46B 15/00* (2013.01); *A46B 2200/1066* (2013.01); *A46B 11/0006* (2013.01); *A46B 11/0068* (2013.01); *A61Q 11/00* (2013.01); *A46B 9/04* (2013.01); *A61K 2800/30* (2013.01); *A61K 2800/87* (2013.01)

(58) Field of Classification Search
CPC .. A46B 9/04; A46B 15/00; A46B 2200/1066; A46D 1/00; A46D 1/02; A46D 1/0207; A46D 1/0269
USPC .............. 15/167.1, 207.2; 428/364, 367, 368, 428/372
See application file for complete search history.

(56) References Cited

U.S. PATENT DOCUMENTS

2009/0092563 A1    4/2009   Alfred et al.

FOREIGN PATENT DOCUMENTS

| JP | 2001-197940 | * | 7/2001 |
|---|---|---|---|
| WO | 98/55001 A1 | | 12/1998 |

* cited by examiner

*Primary Examiner* — Mark Spisich
(74) *Attorney, Agent, or Firm* — Janet Sleath; Speckman Law Group PLLC

(57) ABSTRACT

A dental cleaning system for cleaning the tooth surfaces of patients who have orthodontic braces is provided that enables the possibility of performing daily tooth cleaning without resulting in the occurrence of problematical deposits of abrasive particles on the orthodontic appliances for patients who use orthodontic appliances for correction of a dental, maxillary and/or mandibular malposition, for example, orthodontic braces with an arch wire guided therein. The system includes a non-abrasive toothpaste and a toothbrush having bristles made of synthetic fibers into which activated carbon particles of charcoal with average diameters greater than or equal to 100 μm are incorporated in an amount greater than or equal to 40 vol % of the bristles.

4 Claims, No Drawings

USE OF A TOOTHPASTE AND A TOOTHBRUSH, A DENTAL CLEANING SYSTEM AND TOOTHBRUSH

REFERENCE TO RELATED APPLICATIONS

This application claims priority to Swiss patent application no. 01733/12, filed Sep. 25, 2012.

TECHNICAL FIELD

The present invention describes a system for cleaning the surfaces of the teeth of patients wearing orthodontic braces and a toothbrush comprising bristles made of synthetic fibers.

BACKGROUND OF THE INVENTION

Toothpastes or dentifrices have been in use for a long time to improve the mechanical tooth-cleaning effect while using toothbrushes in various embodiments.

In addition to active ingredients for preventing caries, conventional toothpastes contain a number of different substances, for example, flavorings, preservatives, foaming agents and humectants, which form a soft toothpaste having an attractive appearance and a creamy consistency.

To support the mechanical cleaning of tooth surfaces to eliminate plaque and bacteria, toothpastes today contain a cleaning substance that contains abrasives. These abrasives usually consist of mineral substances in different grain sizes, which have abrasive effects, so that the tooth surfaces can be cleaned in a gentle manner.

For patients who wear orthodontic appliances, in particular braces, tooth cleaning using conventional toothpaste repeatedly results in problematical deposits of toothpaste residues on the orthodontic braces because of the abrasives. The various substances of various grain sizes form unwanted deposits because they can no longer be removed with a toothbrush. The result is a restricted effect because the unwanted deposits reduce the mobility of the arch wires in the orthodontic brace, which has the effect of interfering with the treatment.

To prevent problematical deposits on the movable parts of orthodontic braces, orthodontic patients may rely on non-abrasive toothpastes, i.e., they containing no abrasives. However, the cleaning results are then often inadequate. There have also been attempts to use various abrasives which clean the teeth in a gentle manner but hardly cause any problematical deposits at all.

DE4008995 discloses a toothpaste containing activated carbon powder as an abrasive. The granularity of the activated carbon is selected so that the activated carbon particles have open pores and are fine-grained, with an average diameter between 2 μm and 20 μm, such that the surface development and/or the internal surface area is greater than 300 m$^2$/g. The abrasive effect of the activated carbon particles in a formulation containing between 0.5 wt % and 50 wt % and having the aforementioned grain size is not adequate, so the cleaning results are inadequate for patients having orthodontic braces. In addition, interfering deposits may nevertheless occur on dental clamps because of the minerals such as diatomaceous earth and various carbonates that are still present in the toothpaste as well as the deposits of very small carbon particles per se. This source does not disclose whether the activated carbon particles are from hard coal or charcoal.

To prevent deposits, an attempt may additionally be made to use a mouth wash after toothbrushing. A suitable mouth wash must be discovered and acquired accordingly. It cannot be assumed here that the deposits have been eliminated.

WO2009/045856 describes a special toothbrush having bristles, into which activated carbon particles for example, are incorporated. These activated carbon particles are released from the bristles while brushing the teeth and serve as activators for a bleaching reaction with a bleach present in the toothpaste. A bleaching effect can be achieved from brushing teeth by using the toothbrush and adding activated carbon particles to the toothpaste, which must necessarily contain a bleaching agent. Activated carbon here serves merely as an activator, but no information can be provided about the shape and properties of the activated carbon particles. According to WO2009/045856, the special problems involving patients who use dental clamps are not discussed, and the toothbrush described there is not intended for toothbrushing several times a day.

SUMMARY OF THE INVENTION

The object of the present invention is to create a possibility for performing the daily toothbrushing without any problematical deposits of abrasive particles occurring on the orthodontic appliances for patients who have orthodontic appliances for correction of a dental, mandibular and/or maxillary malposition, for example, of orthodontic braces with the arch wire guided therein. Despite the use of orthodontic appliances, an optimal cleaning of the dental surfaces and orthodontic appliances should be ensured, wherein the mechanics should prevent the development of problematical particle deposits.

This object is achieved by a system comprising a non-abrasive toothpaste and a toothbrush whose bristles contain activated carbon particles of a sufficient size incorporated in such a manner that they can be released.

DETAILED DESCRIPTION

Patients wearing dental appliances for correction of a dental, maxillary and/or mandibular malposition should use a non-abrasive toothpaste. Such a toothpaste would not contain any granular mineral substances as additives which have an abrasive or bleaching effect on the tooth enamel. One such toothpaste is already known under the brand name ZAHNSCHNEE® [dental snow] by the present applicant. In addition, the non-abrasive toothpaste may contain known foaming agents, humectants, flavorings or taste substances as well as preservatives, coloring agents and additives and substances with a prophylactic effect against periodontal disease or caries.

Because of the absence of abrasives in the toothpaste, the ability to eliminate plaque and bacteria from the dental surfaces is present in a reduced form. Abrasives are incorporated into the bristles of a toothbrush in the form of abrasive particles. As is known, such a toothbrush comprises a brush head on which a plurality of bristles may be arranged in different orientations, with differing hardness and with bristle ends of various shapes. The bristles may be manufactured from various synthetic fibers, for example, polyamides such as nylon or polyesters. Those skilled in the art are familiar with materials for producing bristles of varying softness.

Before manufacturing the bristles, the bristle material is mixed with activated carbon particles with average diameters greater than or equal to 100 μm, resulting in a plastic/activated carbon mixture containing activated carbon particles. The activated carbon particles are introduced in the form of powdered charcoal into the bristle material, so that the most homogeneous possible distribution is achieved. A composition of the plastic containing added activated carbon particles, which is later processed to form granules and is ready for further processing, is usually produced.

The bristles are produced by plastic extrusion molding, whereby bristles with diameters of approximately 150 μm to 300 μm are created from the plastic/activated carbon mixture granules with the activated carbon particles distributed in the bristles. The plastic forms a matrix into which the activated carbon particles with an average diameter of 100 μm are incorporated, whereby activated carbon particles are exposed at the bristle heads by corresponding processing and may protrude partially out of the plastic. Bristles containing activated carbon particles in an amount by volume of greater than or equal to 40% ensure that enough activated carbon particles will always be released during use and wear on the bristles.

The average diameter of the activated carbon particles used should amount to approximately 30% to 70% of the bristle diameter, preferably approximately 50% of the bristle diameter.

The activated carbon particles comprise open-pored, fine-grained carbon particles from charcoal having an internal surface area of 300 to 2000 $m^2/g$. Activated carbon particles that can be used here can only be of vegetable origin, and pure carbon is used without the addition of other chemicals.

In addition to an abrasive and cleaning effect, the activated carbon particles have anti-inflammatory, adsorbent and bleaching effects on the tooth surface. Because of the incorporation of the activated carbon particles into the synthetic fiber bristles, the possibility of overdosing of the abrasive is ruled out. The charcoal is an extremely mild abrasive such as that conventionally used for scratchless polishing. Through contact with the toothpaste and mechanical operation of the toothbrush, the activated carbon particles are gradually released at a maximum rate at which no problematical abrasive deposits are formed. Since the abrasives are dissolved out of the bristles directly on the tooth surfaces, the result is a cleaning effect directly at the point of contact of the bristles with the tooth surface. Thus a more targeted application of abrasives is possible in comparison with the use of toothpaste containing activated carbon.

When using an non-abrasive toothpaste with a toothbrush having bristles containing activated carbon particles having an average diameter of greater than or equal to 100 μm in an amount equal to or greater than 40 vol %, individual activated carbon particles are dissolved out of the bristles during toothbrushing and then function as bleaching and polishing particles and thus as abrasives on the tooth surface.

By supplying the activated carbon particles from the matrix of the bristles, a sufficiently large amount of abrasive reaches the tooth surface, thus preventing lumping and the formation of problematical deposits on orthodontic appliances.

The sale of a system comprised of a non-abrasive toothpaste and a toothbrush having bristles furnished with activated carbon particles of a suitable size and distribution accordingly is offered for patients who use dental appliances such as orthodontic braces for correction of a dental, maxillary and/or mandibular malposition. These patients need not obtain additional mouthwashes when using such a system, while nevertheless achieving a cleaning of the dental surfaces without leaving any residues of toothpaste on the orthodontic braces.

The invention claimed is:

1. A dental cleaning system for cleaning the tooth surfaces of patients with orthodontic braces, comprising a non-abrasive toothpaste and a toothbrush having bristles made of synthetic fibers into which activated carbon particles from charcoal with average diameters of greater than or equal to 100 μm are incorporated in an amount greater than or equal to 40 vol %.

2. The dental cleaning system according to claim 1, wherein the average diameter of the activated carbon particles from charcoal amounts to approximately 30% to 70% of the diameter of the bristles.

3. A toothbrush comprising bristles of synthetic fibers, wherein activated carbon particles from charcoal having average diameters greater than or equal to 100 μm are incorporated into the synthetic fibers, wherein the amount of activated carbon particles in the bristles is greater than or equal to 40 vol %.

4. The toothbrush according to claim 3, wherein the average diameter of the activated carbon particles from charcoal amounts to approximately 30% to 70% of the diameter of the bristles.

* * * * *

UNITED STATES PATENT AND TRADEMARK OFFICE
CERTIFICATE OF CORRECTION

PATENT NO. : 9,032,581 B2  Page 1 of 1
APPLICATION NO. : 14/035838
DATED : May 19, 2015
INVENTOR(S) : Roland Zettel It is certified that error appears in the above-identified patent and that said Letters Patent is hereby corrected as shown below:

| Col. No. | Line(s) | Edits |
|---|---|---|
| Title Page | Item 73 | Replace "Tuefen" with --Teufen-- |

Signed and Sealed this
Second Day of February, 2016

Michelle K. Lee
*Director of the United States Patent and Trademark Office*